United States Patent [19]
Tamburrino et al.

[11] Patent Number: 5,512,036
[45] Date of Patent: Apr. 30, 1996

[54] DENTAL IMAGING SYSTEM

[75] Inventors: Richard A. Tamburrino, Auburn; Roger W. Leseberg, Liverpool, both of N.Y.

[73] Assignee: Welch Allyn, Inc., Skaneateles Falls, N.Y.

[21] Appl. No.: 213,677

[22] Filed: Mar. 15, 1994

[51] Int. Cl.$^6$ .................................. A61B 1/05; A61B 1/06
[52] U.S. Cl. ................................................ 600/172; 433/29
[58] Field of Search .......................... 433/29, 31; 128/4, 128/6; 600/112, 137, 160, 172

[56] References Cited

U.S. PATENT DOCUMENTS

| | | | |
|---|---|---|---|
| 4,552,131 | 11/1985 | Omagari | 128/6 |
| 4,704,007 | 11/1987 | Landre et al. | 128/4 |
| 4,998,182 | 3/1991 | Krauter et al. | 361/394 |
| 5,049,070 | 9/1991 | Ademovic | 433/29 |
| 5,124,797 | 6/1992 | Williams et al. | 433/29 |
| 5,251,613 | 10/1993 | Adair | 128/6 |
| 5,408,992 | 4/1995 | Hamlin et al. | 128/6 |

FOREIGN PATENT DOCUMENTS

| | | | |
|---|---|---|---|
| 3339669 | 5/1985 | Germany | 433/29 |

*Primary Examiner*—Cary E. O'Connor
*Attorney, Agent, or Firm*—Harris Beach & Wilcox

[57] ABSTRACT

An imaging system has an optical assembly that can be removably attached to an elongated housing for insertion therewith into a narrow orifice. The housing has an imager such as a CCD array disposed therein. The housing and the optical assembly are secured together by a bayonet connector that is centered on the distal end of the housing. The housing has a plurality of light guides for transmitting light energy through the distal end of the housing via ports that are radially more distant from the axis of the housing than the outermost surface of the bayonet connector. The optical assembly has passages that align with the light guides of the housing, so that light energy passes from the light guides in the housing through the optical assembly along pathways that are outboard of the bayonet connector. The system can be employed for dental imaging, wherein the housing has an elliptical profile and is dimensioned to fit in the mouth of a patient. The housing further has a smooth, continuous exterior surface for receiving a protective sheath thereon. The exterior surface of the optical adapter is aligned with the exterior surface of the housing so that the unit has a smoothly continuous surface.

10 Claims, 4 Drawing Sheets

DENTAL IMAGING SYSTEM

BACKGROUND OF THE INVENTION

1. Field of the Invention

This invention relates to imaging devices for the inspection of poorly accessible locations. More particularly this invention relates to an imaging system suitable for dental applications wherein it is desirable to interchange optical assemblies.

2. Description of the Prior Art

Borescopes and endoscopes are well known imaging apparatus utilizing charge coupled devices (CCD) as photosensors. In the art of dental imaging, similar devices exist; however this application has specialized requirements that are not well met in the prior art devices. It is desirable that a dental imager possess a continuous low profile for ease of manual manipulation, and the device must be accommodated in the mouth of a dental patient. A removable protective sheath must readily slip on and off the device to maintain hygiene and prevent the transmission of disease between patients. A smooth continuous outer surface is important to this end. Finally, as the dental structures need to be visualized from various perspectives, and at different magnifications, it is desirable that the device accept interchangeable optical assemblies, without increasing the size of the device's profile or disturbing the smooth continuity of its exterior surface.

SUMMARY OF THE INVENTION

It is therefore a primary object of the present invention to provide an improved dental imaging instrument that has a small profile, and can accept interchangeable optics for viewing dental structures at different angles and magnifications.

It is another object of the present invention to provide an improved dental imaging instrument having interchangeable optics that is easily controlled manually and that can be covered by a removable protective sheath.

These and other objects of the present invention are attained by an imaging system of the type having an optical assembly that can be removably attached to an elongated housing for insertion therewith into a narrow orifice. The housing has an imager such as a CCD array disposed therein. A connector is centered on the distal end of the housing and has a radially outermost surface. The removable optical assembly is adapted to mate with the connector, such that the optics within the assembly and projects an image of a target being viewed onto the imager. The housing has at least one illuminator which transmits light energy through the distal end of the housing via ports that are farther from the axis than the outermost surface of the connector.

In one aspect of the invention the illuminator comprises a first light guide disposed within the housing that extends to the distal face for transmitting light rays therethrough. The optical assembly has a second light guide formed therein that aligns with the first light guide so that light energy continues therethrough to illuminate the target being viewed.

In another aspect of the invention the connector and the optical assembly are provided with a bayonet fitting for achieving a secure connection therebetween. The connector is provided with an outwardly directed cylindrical rim having a plurality of bayonet tracks formed therein, and the optical assembly has a recess dimensioned to snugly receive the cylindrical rim. A plurality of bayonet pins project inwardly from a wall of the recess and are carried in the bayonet tracks. The bayonet tracks each have a first arm that has a generally longitudinal orientation and a second arm that has a generally cross-longitudinal orientation.

The system can be employed for dental imaging, wherein the housing has an elliptical profile and is dimensioned to fit in the mouth of a patient. The housing further has a smooth, continuous exterior surface for receiving a protective sheath thereon. The exterior surface of the optical adapter is aligned with the exterior surface of the housing to form a smoothly continuous surface.

BRIEF DESCRIPTION OF THE DRAWING

For a better understanding of these and other objects of the present invention, reference is made to the detailed description of the invention which is to be read in conjunction with the following drawings, wherein.

DESCRIPTION OF THE PREFERRED EMBODIMENT

Figure 1:
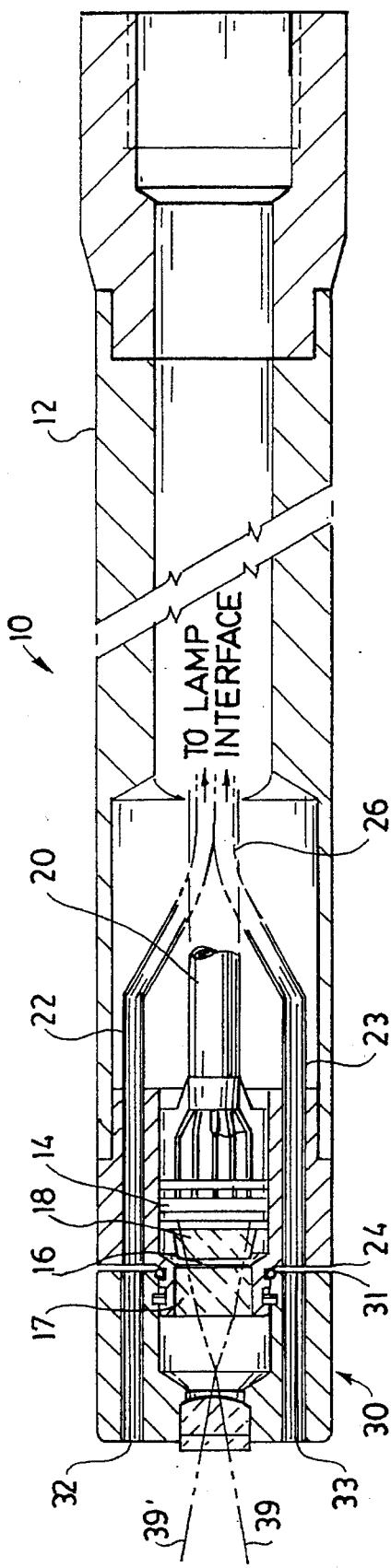
FIG. 1 is a sectional view of an imaging system in accordance with the present invention with an optical assembly attached.

Turning now to FIG. 1 of the Drawing an imaging system 10 is shown in accordance with the invention. While system 10 is described in the context of dental imaging, the invention is not limited to this application, and can be practiced whenever interchangeable optics are required in a borescope that is required to have a small profile. System 10 includes a housing 12 that has a smooth external surface and is preferably elliptical in profile. It has been found that an elliptical shape promotes grasping with the hand during manual manipulation of the device in the mouth of a patient.

Disposed in the distal portion of the housing 12 is a compact imager 14 which is preferably a packaged charge-coupled device supplied with integrated electronics, and having a transparent window 16 at its distal end that permits an image to be focused upon an photosensitive area of the imager 14. A suitable window is provided in the distal end 24 of the housing to permit light to pass therethrough and into the imager 14. A plurality of connector pins 18 extend proximally from the imager 14 to join an electrical harness 20 that carries necessary power and input signals to the imager 14, and carries output signals from the imager to video processing electronics (not shown).

Figure 9:
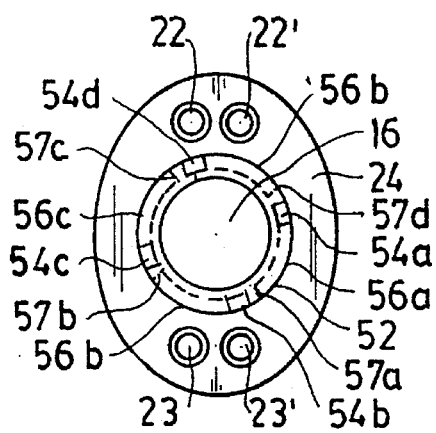
FIG. 9 is a plan view of the connector in the assembly of FIG. 1 with the optical assembly removed.

In FIGS. 1 and 9 are shown a plurality of light guides 22, 22', 23, 23'. The light guides are disposed between the exterior wall of the housing 12 and the imager 14. Beginning at the distal face 24 of the housing 12, they run proximally in a generally longitudinal direction, turning medially to unite in a common bundle 26 which runs proximally toward a light source (not shown) which typically is a high intensity metal halide discharge lamp.

Power can be supplied to the imager 14 and to the lamp from a battery (not shown) disposed in the housing 12, or from an external source.

Figure 10:
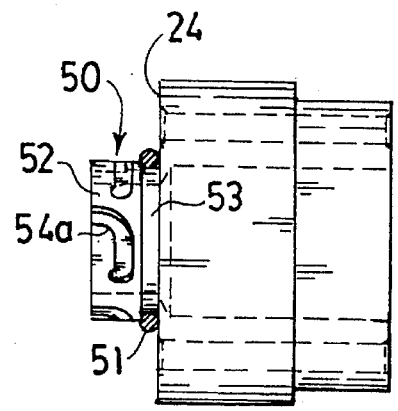
FIG. 10 is a side elevation of the connector shown in FIG. 9.
Figure 11:
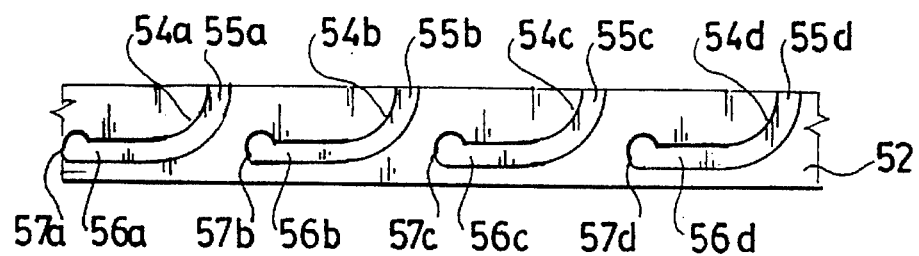
FIG. 11 is a flat projection of the distal portion of the connector shown in FIG. 10.
Figure 12:
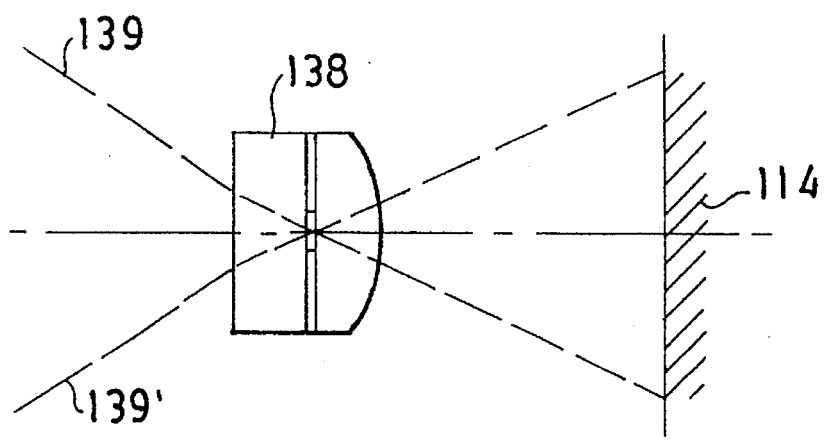
FIG. 12 is a diagram of an optical arrangement in an imaging system in accordance with the prior art.
Figure 13:
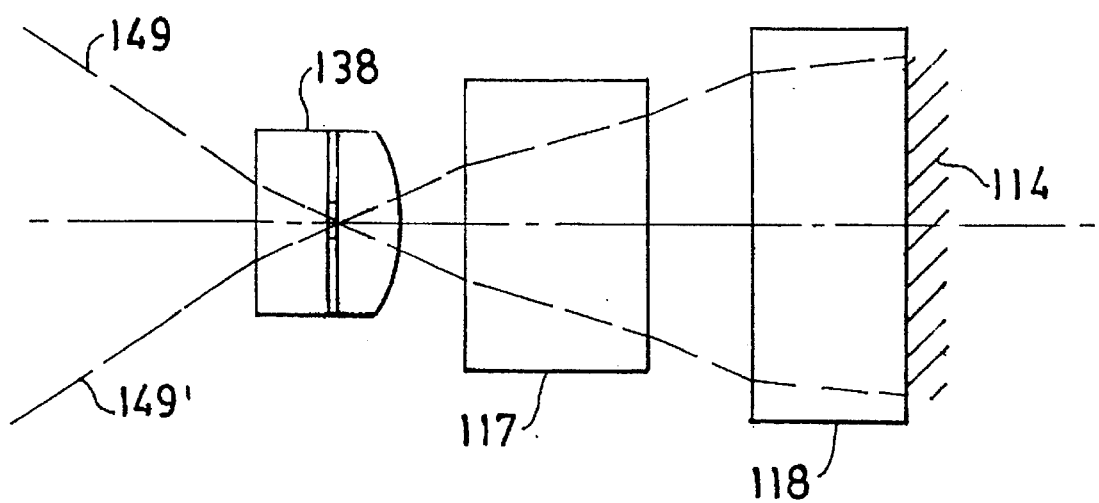
FIG. 13 is a diagram of an optical arrangement in an imaging system in accordance with the invention.

As best seen in FIGS. 9–11, a outstanding bayonet adapter 50 extends distally beyond the distal face 24. It has a cylindrical outer wall 52 disposed inwardly of the light guides 22, 22', 23, 23', which attaches to the distal face 24 of the housing 12. An o-ring 51 seats in a groove 53 located at the base of the bayonet adapter 50. Its function is to aid in locking the bayonet connection and retaining the optical assembly. A plurality of bayonet tracks 54a–54d are placed at intervals along the circumference of the rim 52. Each track has a relatively short longitudinal arm 55a–55d and a longer cross-longitudinal arm 56a–56d. Inside the cylinder 52, light can pass through the transparent plate 16. As best seen in FIG. 1, the light then passes through two windows 16, 17 that are made of a glass having a high refractive index to strike the photosensitive area of the imager 14. A glass having a refractive index Nd=1.85, such as LaSF9, available from Schott Optical Glass, Inc., Duryea Pa., is suitable. The windows 16, 17 are an important feature of the invention. Their presence allows the physical distance between the objective lens 38 and the imager 14 to be long enough to allow the bayonet mechanism to be placed in the receive path, where it can be made smaller than the elliptical cross section of the distal face 24. The fabrication of windows 16, 17 of high index glass allows significant lengthening of the physical distance between the lens and the imager, and permits a wide field of view. This can be appreciated with reference to FIGS. 12 and 13. In FIG. 12 there is shown schematically an arrangement that is found in prior art imaging systems, in which an objective lens system 138 is disposed in front of a CCD imager 114. Principal rays 139, 139' pass through the lens system 138 and are transmitted to the active region of the imager 114. In FIG. 13 there is shown schematically an optical arrangement in accordance with the invention, in which the same lens system 138 receives principal rays 149, 149'. The rays 149, 149' define the same field of view as the rays 139, 139' of FIG. 12, and they pass through the lens 138 in the same manner as in the prior art arrangement of FIG. 12. But now rays 149, 149' pass in turn through windows 117, 118, which are made of a high index glass that refracts the rays inward. When the rays 149, 149' finally strike the same active area of 114 as did rays 139, 139', it will be evident that they have traveled a larger longitudinal distance measured between the lens 138 and the imager 114. The bayonet adapter 50 can be interposed therebetween in the arrangement of FIG. 13, whereas this could not practically be done in FIG. 12 without compromising the system's optical performance.

Figure 2:
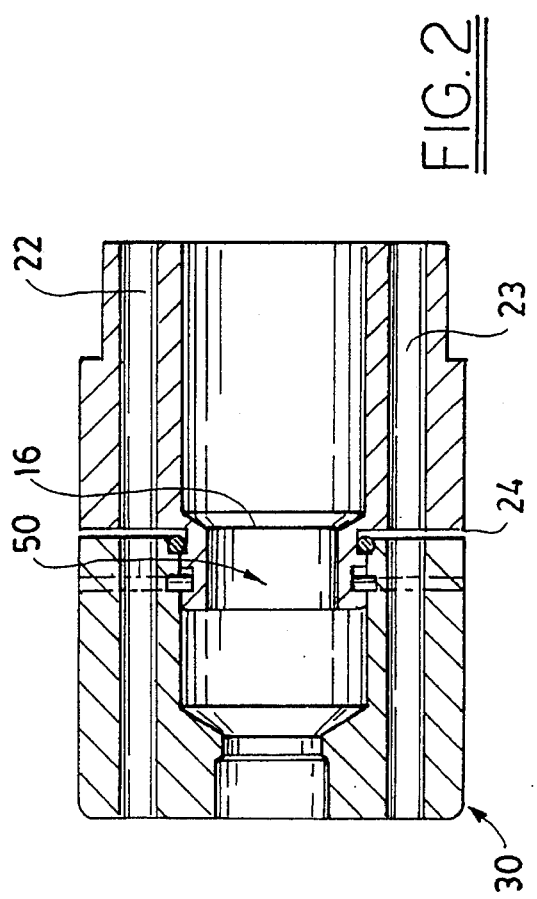
FIG. 2 in an enlarged view of the connection of the optical assembly with the embodiment of FIG. 1 with certain details omitted.
Figure 3:
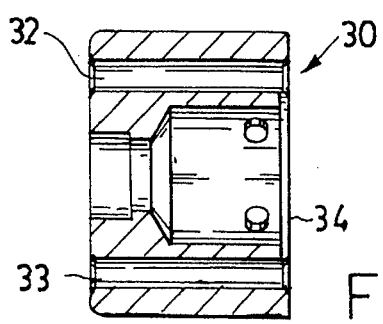
FIG. 3 is a sectional view through line 3—3 of FIG. 4.
Figure 4:
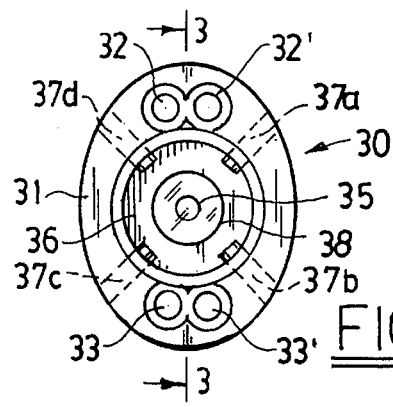
FIG. 4 is a plan view of the optical assembly shown in FIG. 1.

FIGS. 3 and 4 show a removable optical assembly 30 that is adapted to the bayonet adapter 50. Optical assembly 30 has an elliptical body profile corresponding to that of the distal face 24 of the housing 12. As best shown in FIG. 2, when the assembly 30 is mounted on the housing 12 its proximal face 31 bears on the distal face 24 of the housing 12, and passages 32, 33 align with light guides 22, 23. Passages 32', 33' also align with other light guides (not shown) inside the housing 12. Light passing distally through the light guides 22, 23 can thus continue unimpeded through the optical assembly 30 toward a target located beyond the distal face 34. Dimensions of the preferred embodiment are shown in Tables 1 and 2.

TABLE 1

|  | longitudinal thickness (mm) |
| --- | --- |
| Window 17 | 3.6 |
| Window 16 | 2.0 |
| inter-window Separation | 0.58 |

TABLE 2

| Distal Face of Housing | dimension (mm) |
| --- | --- |
| Major Axis | 17.0 |
| Minor Axis | 13.2 |
| Bayonet Adapter 50 external diameter | 8.0 |
| Bayonet Adapter 50 internal diameter | 5.8 |

With reference to FIG. 4 the optical assembly 30 has a central aperture 35 bored therethrough and a lens 38 placed therein. Lens 38 can be any lens or combination of lenses as are known to the art in order to achieve desired optical characteristics such as magnification, field of view, field correction, and the like. A cylindrical recess or well 36 is formed in the proximal face 31. The well 36 has a somewhat larger diameter than the central aperture 35 and is concentric therewith. It is important that the well 36 be located inboard of the passages 32, 32' and 33, 33', so that the distance between the central axis of the well 36 and the closest wall of each of the passages 32, 32', 33, 33' exceeds the radius of the well 36. This assures that light travelling through the passages 32, 32', 33, 33' never enters the well 36. The primary purpose of this inboard arrangement of the bayonet adapter is to minimize the major and minor axes of the elliptical profile of the housing. Other purposes are to prevent light loss within the system 10, and to block internal light paths between the passages 32, 32', 33, 33' and the imager 14.

A plurality of bayonet pins 37a–37d are directed radially toward the center of the well 36. The ends of the bayonet pins 37a–37d protrude inwardly through the wall of the well 36. The well 36 is dimensioned to snugly receive the bayonet adapter 50, and the bayonet pins 37a–37d align with the longitudinal arms 55a–55d of the bayonet tracks 54a–54d respectively. Referring again to FIGS. 9–11, when the bayonet adapter 50 is received in the well 36, the bayonet pins 37a–37d are initially carried by the longitudinal arms 55a–55d. When the bayonet pins reach the proximal end of the longitudinal arms, a twisting motion is imparted between the now partially engaged optical assembly 30 and the housing 12, so that the two rotate in opposite directions relative to one another about their common central axis. This causes the bayonet pins 37a–37d to slide along the cross-longitudinal arms 56a–56d respectively and seat in the terminal indents 57a–57d thereof. This fully engages the optical assembly 30. It is evident that the optical assembly 30 is restrained from longitudinal detachment by the bayonet pins 37a–37d. Pressure transmitted against the proximal face 31 of the optical assembly 30 by the distal face 24 of the housing, working through the resilient o-ring 51 assists the locking engagement of the pins 37a–37d in the indents 57a–57d. This prevents undesired rotation of the optical assembly 30 about its axis.

When the optical assembly 30 is thus mounted on the housing 12, the system 10 has a smooth, continuous exterior surface, over which a protective sheath or condom (not shown) can be readily slipped on and off. Actuation of the light source causes light to pass through the bundle 26, light guides 22, 23, and passages 32, 33. Of course light also passes through other light guides (not shown) and through passages 32',33' to illuminate a target therebeyond. Scattered and reflected light from the target returns to the system in a receive path, representatively indicated by rays 39, 39' in FIG. 1. The receive path passes through the central aperture 35, lens 38, and the interior of well 36. The receive path continues across the proximal face 31 of the optical assembly 30, and enters the housing 12 through its distal end 24. It then passes through the transparent window 16 of the imager 14, and is refracted by windows 17, 16 to terminate on the photosensitive area of the imager. After the output signal developed by the imager 14 in response to light incident thereon is processed in a known manner, the target can be visualized by the user on a monitor or other suitable display.

The optical assembly 30 can be detached from the housing 12 by reversing the steps required to mount it. A reverse twisting motion is first imparted to the optical assembly 30 and the housing 20, so that the two rotate relative to one another about their common central axis, the bayonet pins 37a–37d sliding in the bayonet tracks 54a–54d until the longitudinal arms 55a–55d are reached. The optical assembly 30 is then longitudinally withdrawn from engagement with the bayonet adapter 50. As this occurs the bayonet pins 37a–37d slide in the longitudinal arms 55a–55d of the bayonet tracks 54a–54d.

Figure 5:
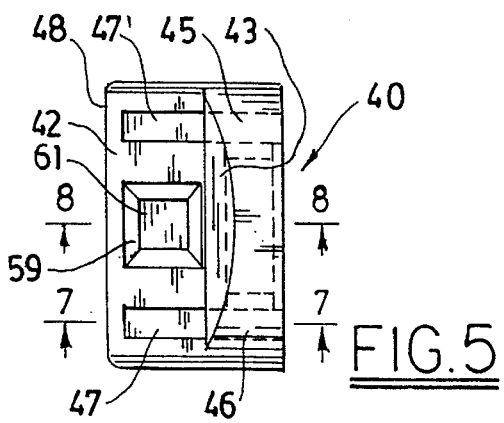
FIG. 5 is a side elevation of another optical assembly that can be substituted for the assembly of FIG. 4.
Figure 6:
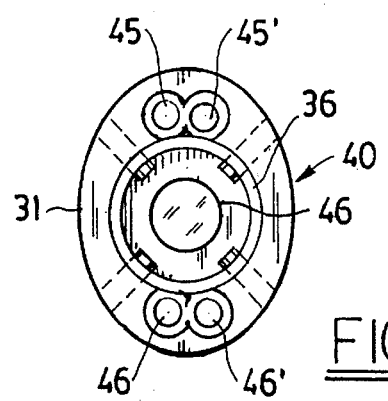
FIG. 6 is a plan view of the optical assembly of FIG.
Figure 7:
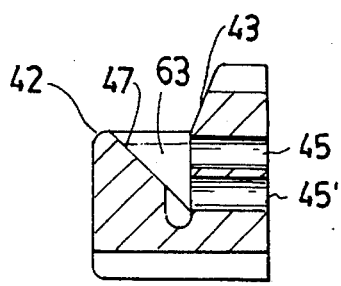
FIG. 7 is a sectional view through line 7—7 of FIG. 5.
Figure 8:
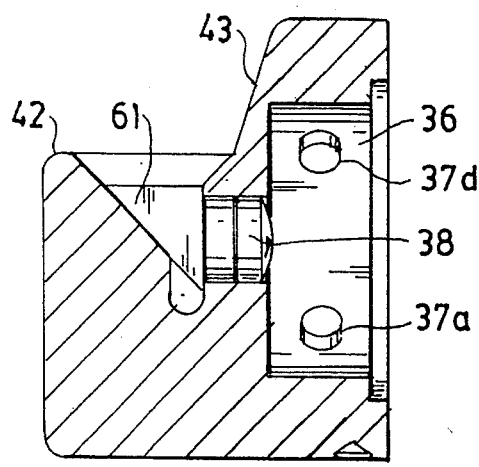
FIG. 8 is a sectional view through line 8—8 of FIG. 5.

Turning now to FIGS. 5 and 6, there is shown another optical assembly 40 which is designed for side viewing. In FIGS. 3–6 like components are designated by the same reference numerals. Optical assembly 40 has a generally cylindrical shape. Its proximal portion has the same construction as optical assembly 30, and the details are therefore omitted for brevity. The distal portion of optical assembly 40 has a sideward facing shoulder 42 which terminates proximally at a steeply inclined face 43. A central bore 46 extends beyond the bottom of well 36 and terminates at an intersection with a notch 59 that debouches onto the surface of the shoulder 42. Passages 45, 45', 46, 46' are positioned much the same as passages 32, 32', 33, 33' in optical assembly 30, except that they terminate at the base of the face 43, rather than extending to the distal end 48 of the optical assembly 40. The distal ends of passages 45, 45' communicate with the surface of shoulder 42 via notches 47, 47', best seen in FIGS. 5 and 7. An illuminating prism 63 (see FIG. 7) is placed in each of the notches 47, 47' for redirecting light passing through passages 45, 45' in the desired sideward direction. Similarly, an imaging prism 61 (see FIG. 8) occupies the notch 59 for redirecting light returning from the target through lens 38 and toward the proximal end of the optical assembly 40. Optical assembly 40 is mounted and dismounted in the same manner as optical assembly 30.

To use the system, a chosen optical assembly, such as optical assembly 30, or optical assembly 40 is mounted on the housing 12, and a protective sheath slipped over the optical assembly and the housing. The lamp is actuated by a suitable switch (not shown), and the device positioned in the mouth of a patient. When it is desired to obtain a different view of the dental structures, the sheath is removed. The process is then repeated with another optical assembly.

While this invention has been explained with reference to the structure disclosed herein, it is not confined to the details set forth and this application is intended to cover any modifications and changes as may come within the scope of the following claims:

What is claimed is:

1. An imaging system of the type having a removable optical assembly, comprising: an elongated housing for insertion into a narrow orifice, said housing having a longitudinal axis, a distal face of said housing having an inner area centered on said longitudinal axis;

an imager disposed in said housing;

a connector disposed on said inner area and having a radially outermost surface;

a removable optical assembly adapted to mate with said connector for projecting an image of a target onto said imager;

at least one means for illuminating said target, each said means for illuminating being farther from said axis than said outermost surface of said connector.

2. The system according to claim 1, wherein said means for illuminating comprises a first light guide disposed within said housing that extends to said distal face for transmitting light rays therethrough.

3. The system according to claim 2, wherein said optical assembly has a second light guide formed therein that aligns with said first light guide; whereby the light rays continue therethrough toward the target.

4. The system according to claim 1, wherein said connector and said optical assembly are provided with a bayonet fitting for achieving a secure connection therebetween.

5. The system according to claim 1, wherein said connector is provided with an outwardly directed cylindrical rim having a plurality of bayonet tracks formed therein, and said optical assembly has a recess dimensioned to snugly receive said cylindrical rim, a plurality of bayonet pins projecting inwardly from a wall of said recess and being carried in said bayonet tracks.

6. The system in accordance with claim 5, wherein said bayonet tracks each have a first arm that has a generally longitudinal orientation and a second arm that has a generally cross-longitudinal orientation.

7. A dental imaging system, comprising:

an elongated housing, dimensioned to fit in the mouth of a patient, and having a longitudinal axis and a smooth, continuous exterior surface for receiving a protective sheath thereon;

an electronic imager disposed in said housing;

a removable optical assembly for projecting an image of a target onto said imager;

a bayonet adapter disposed on a distal end of said housing for engaging said optical assembly in secure connection therewith, said bayonet adapter having a radially outermost surface;

a first plurality of light guides disposed in said housing and terminating at said distal end for passage of light rays therethrough to illuminate said target, a first distance radially measured from said longitudinal axis to a said light guide exceeding a second distance radially measured from said longitudinal axis to an outer surface of said bayonet adapter.

8. The system according to claim 7, wherein said electronic imager comprises a CCD array.

9. The system in accordance with claim 8, wherein said housing has an elliptical profile, and an exterior surface of said optical adapter is aligned with said exterior surface of said housing to form a smoothly continuous surface.

10. The system according to claim 7, wherein said bayonet adapter comprises an outwardly directed cylindrical rim having a plurality of bayonet tracks formed therein, and said optical assembly has a recess that is dimensioned to snugly receive said cylindrical rim, a plurality of bayonet pins projecting inwardly from a wall of said recess and being carried in said bayonet tracks.

* * * * *